US009241810B1

(12) United States Patent
Rumi et al.

(10) Patent No.: US 9,241,810 B1
(45) Date of Patent: Jan. 26, 2016

(54) FUSION DEVICE AND ASSOCIATED METHODS

(75) Inventors: Mustasim Rumi, Austin, TX (US); Robert J. Jones, Cedar Park, TX (US); Richard Kana, Lexington, TX (US); John Rossman, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 0 days.

(21) Appl. No.: 13/135,675

(22) Filed: Jul. 12, 2011

Related U.S. Application Data

(60) Provisional application No. 61/363,641, filed on Jul. 12, 2010.

(51) Int. Cl.
*A61F 2/44* (2006.01)
(52) U.S. Cl.
CPC . *A61F 2/447* (2013.01); *A61F 2/44* (2013.01); *A61F 2/4455* (2013.01); *A61F 2002/4475* (2013.01)
(58) Field of Classification Search
CPC ......... A61F 2/4455; A61F 2/447; A61F 2/44; A61F 2002/4475
USPC ............................................ 623/17.11–17.16
See application file for complete search history.

(56) References Cited

U.S. PATENT DOCUMENTS

| | | | | |
|---|---|---|---|---|
| 5,192,327 A * | 3/1993 | Brantigan | .................. | 623/17.11 |
| 6,371,989 B1 * | 4/2002 | Chauvin et al. | ............ | 623/17.11 |
| 6,436,140 B1 * | 8/2002 | Liu et al. | .................... | 623/17.11 |
| 6,562,074 B2 * | 5/2003 | Gerbec et al. | ............... | 623/17.15 |
| 2003/0191531 A1 * | 10/2003 | Berry et al. | ................ | 623/17.11 |
| 2006/0074488 A1 * | 4/2006 | Abdou | ........................ | 623/17.11 |
| 2006/0129244 A1 * | 6/2006 | Ensign | ....................... | 623/17.16 |
| 2007/0270968 A1 * | 11/2007 | Baynham et al. | .......... | 623/17.11 |
| 2008/0082173 A1 * | 4/2008 | Delurio et al. | ............. | 623/17.16 |
| 2008/0249569 A1 * | 10/2008 | Waugh et al. | ................. | 606/249 |
| 2008/0249622 A1 * | 10/2008 | Gray | ........................... | 623/17.11 |
| 2008/0294262 A1 * | 11/2008 | Levieux | ..................... | 623/17.16 |
| 2008/0306596 A1 * | 12/2008 | Jones et al. | ................ | 623/17.16 |
| 2009/0105830 A1 * | 4/2009 | Jones et al. | ................ | 623/17.16 |

* cited by examiner

*Primary Examiner* — Eduardo C Robert
*Assistant Examiner* — Julianna N Harvey
(74) *Attorney, Agent, or Firm* — Winstead PC

(57) ABSTRACT

An interbody fusion device for fusion of vertebrae, and methods thereof. The device includes a first piece made of titanium having upper and lower surfaces configured to engage the endplates of two opposing vertebrae. The upper and lower surfaces include a plurality of barbed teeth configured to engage an endplate. The first piece includes an inner void area configured to receive a second piece. The second piece is configured to engage the first piece to slide over inner surfaces of the first piece become seated and mated in the first piece. The first and second pieces mate to form an assembled interbody fusion device that fits between two vertebrae.

10 Claims, 5 Drawing Sheets

FUSION DEVICE AND ASSOCIATED METHODS

This application claims priority to U.S. provisional application Ser. No. 61/363,641 filed Jul. 12, 2010, incorporated herein in its entirety by reference.

BACKGROUND OF INVENTION

This disclosure relates to the field of spinal fusion. In particular, this disclosure is drawn to spinal fusion devices and associated methods.

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent further damage.

One procedure that is often used to treat back pain or spinal damage is spinal fusion. Spinal fusion is a surgical technique used to fuse two or more adjacent vertebrae. Supplemental bone tissue is typically used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

SUMMARY OF INVENTION

This disclosure relates to spinal fusion implants and related spinal fusion procedures for use in cervical, thoracic and lumbar applications. One type of spinal fusion is interbody fusion. Typically, an interbody fusion procedure places a bone graft between two adjacent vertebrae in the area normally occupied by an intervertebral disc. In preparation for a spinal fusion procedure, at least a portion of the intervertebral disc is removed (often a portion of the annulus is not removed). A device may be placed between the vertebra to maintain spine alignment and disc height. Fusion then occurs between the endplates of the vertebrae.

Generally, this disclosure describes an interbody fusion device that may be used for cervical, thoracic and lumbar interbody fusion. In one example, an interbody fusion device is a load bearing device shaped to fit between adjacent vertebrae in the location of the intervertebral disc. An opening is formed in the device between the upper and lower surfaces that can be filled with a material that will help to facilitate fusion of the vertebrae. In one example, the interbody fusion device is formed by two pieces, as described below.

DETAILED DESCRIPTION

Figure 1:
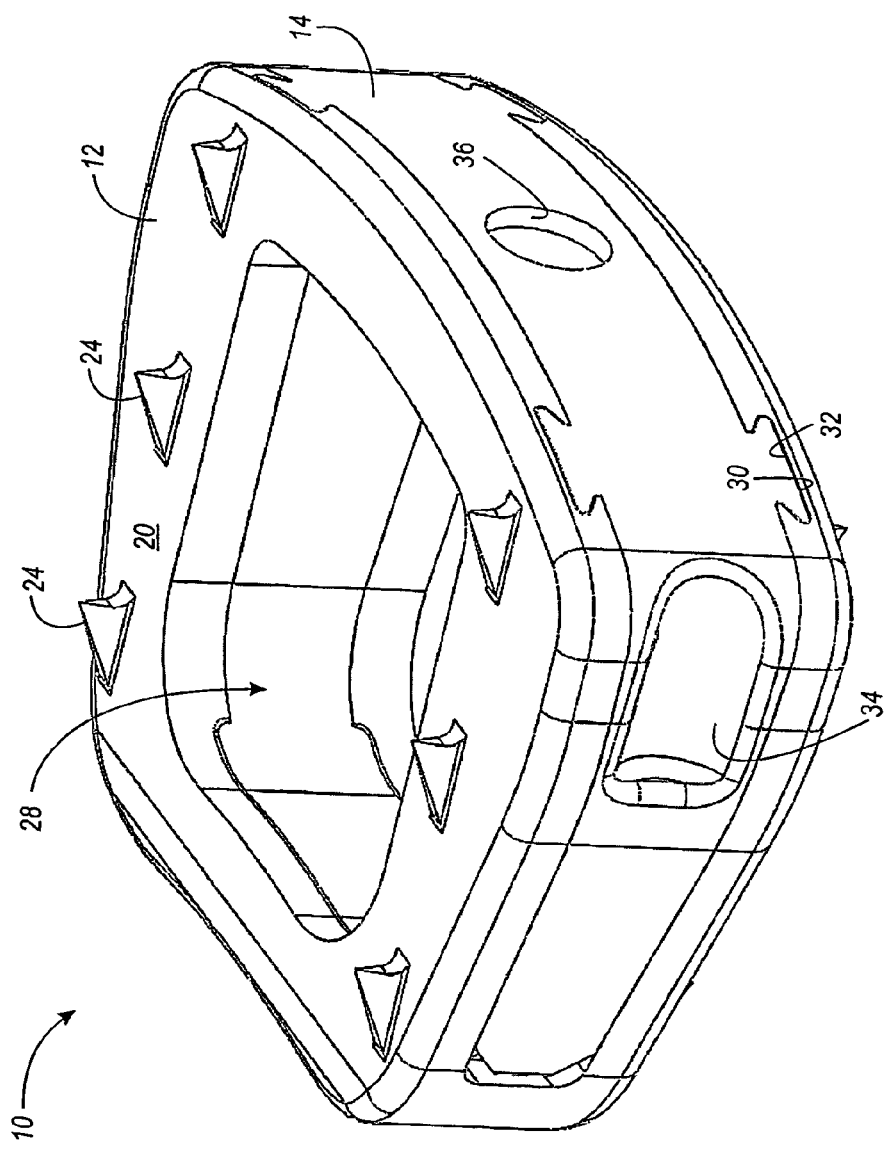
FIG. 1 is an isometric view of one example of an interbody fusion device 10.
Figure 2:
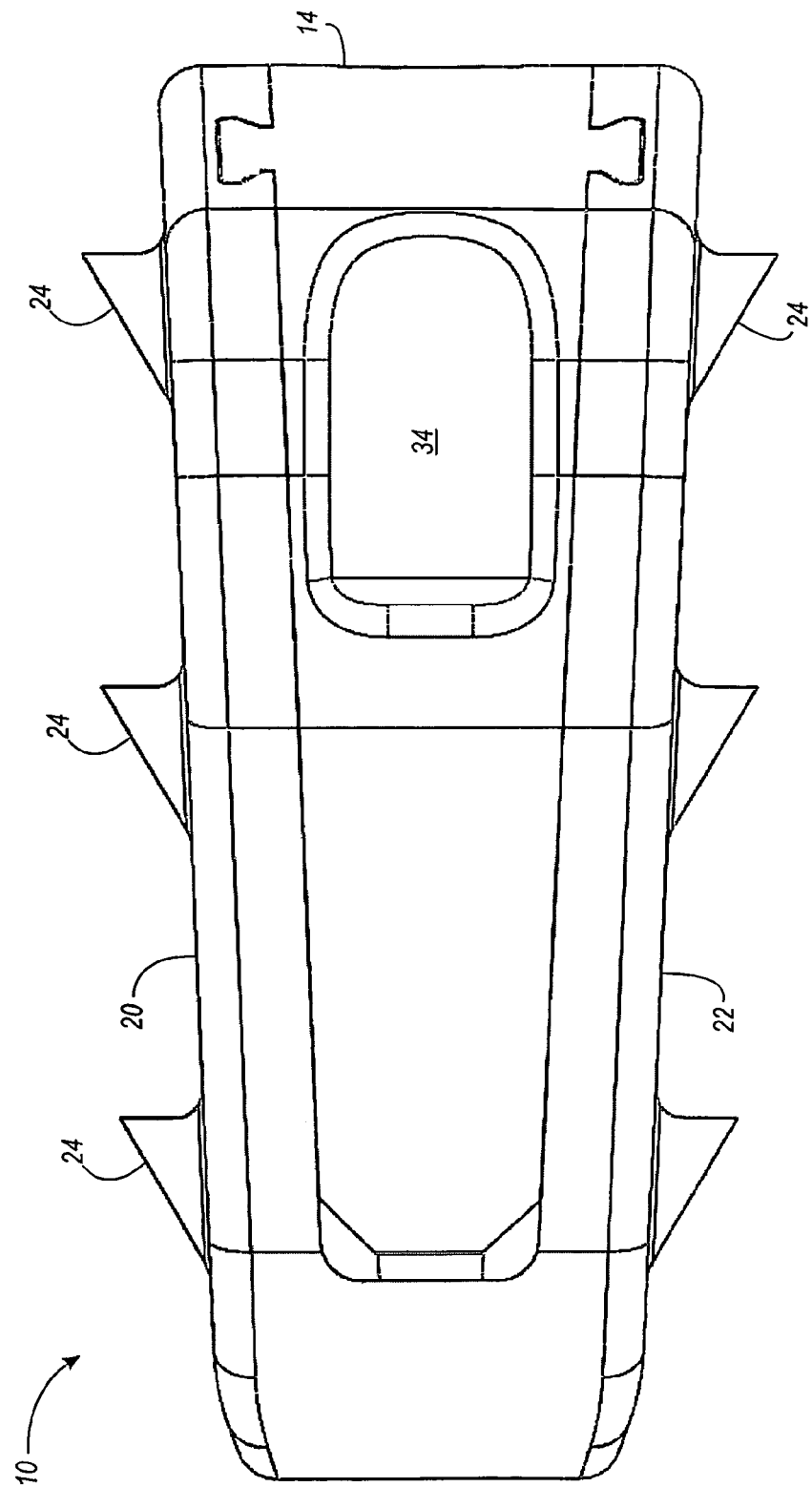
FIG. 2 is a side view of the interbody fusion device 10.
Figure 3:
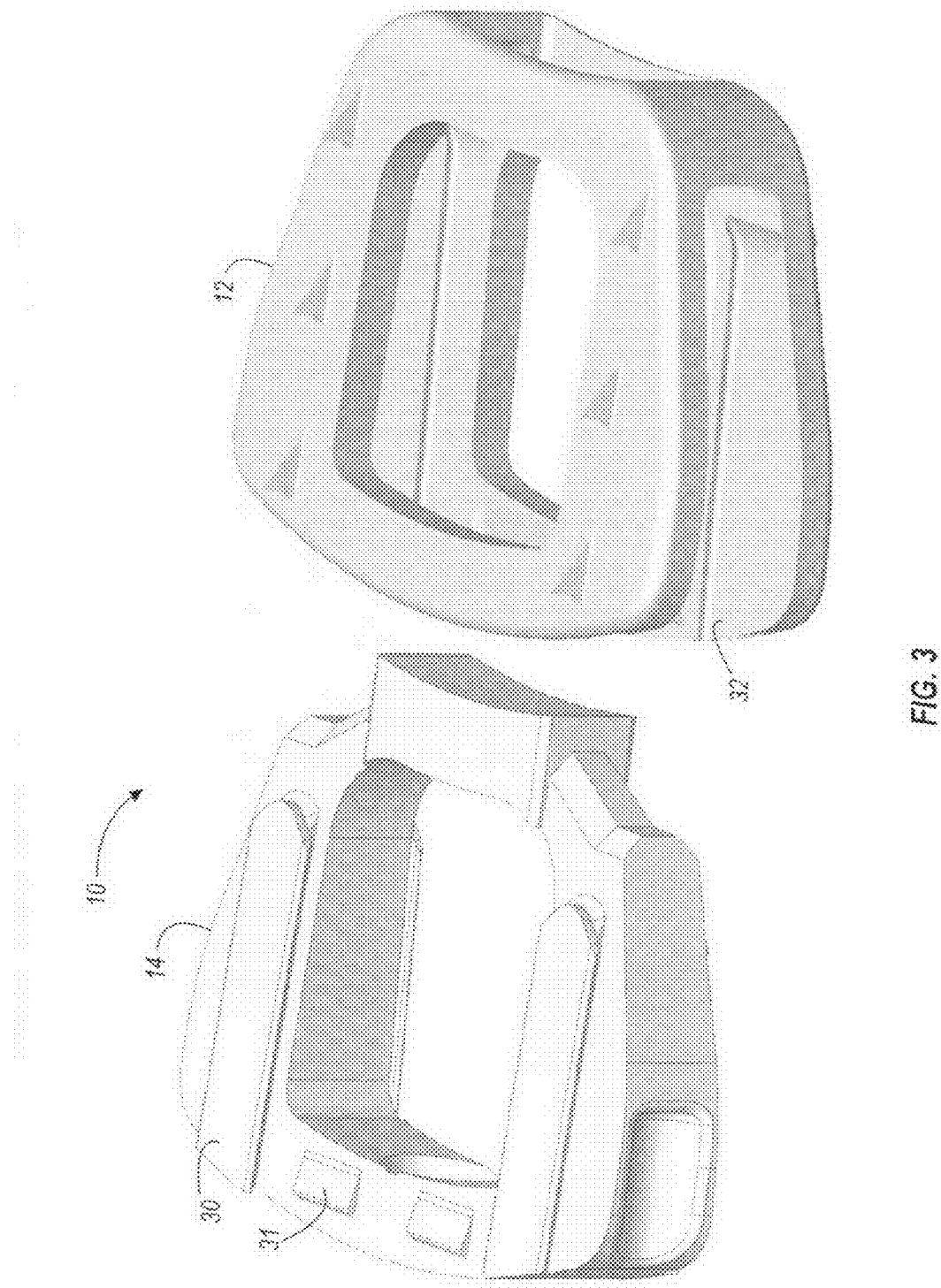
FIG. 3 is an exploded isometric view of the interbody fusion device 10.
Figure 4:
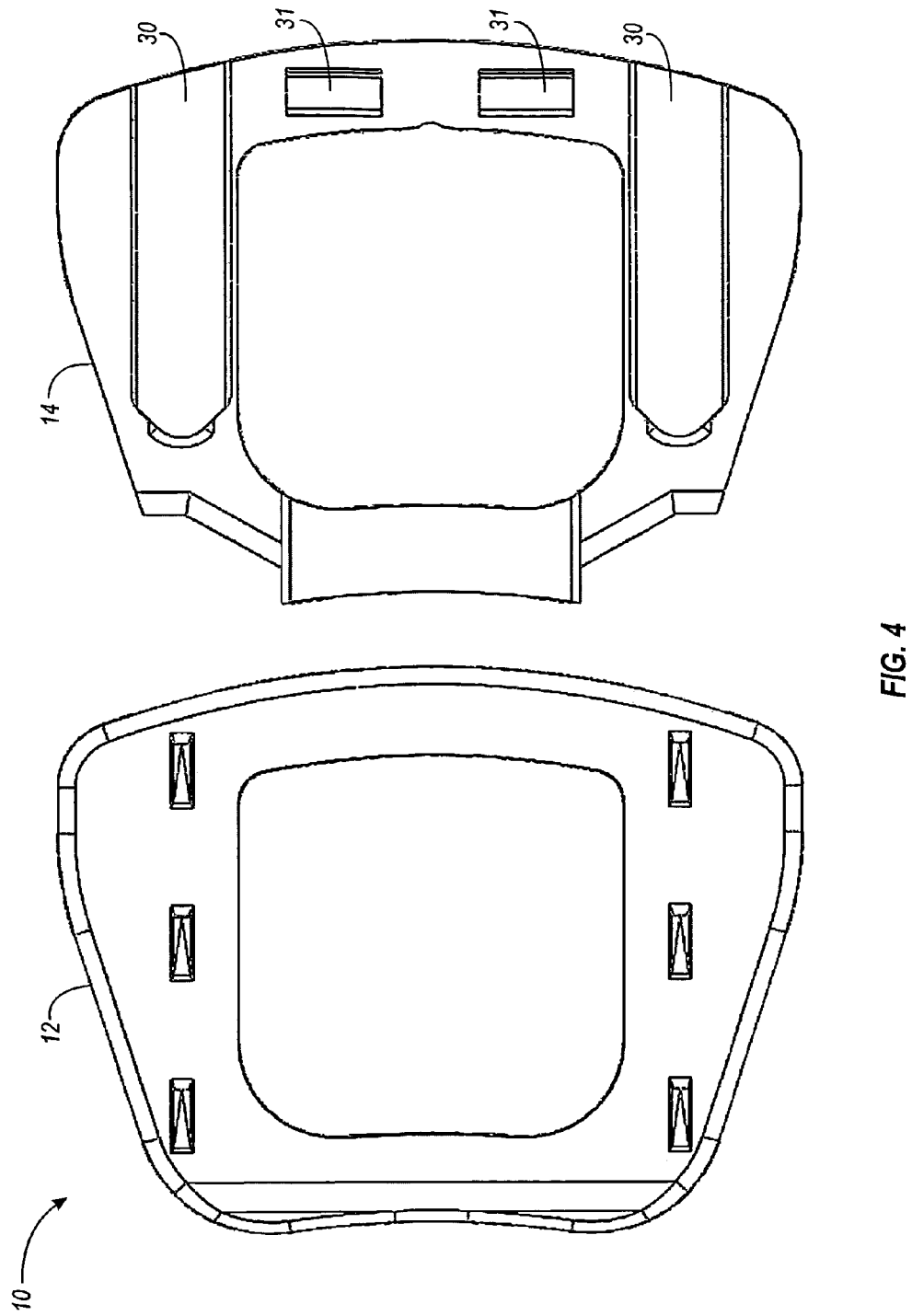
FIG. 4 is an exploded top view of the interbody fusion device 10.
Figure 5:
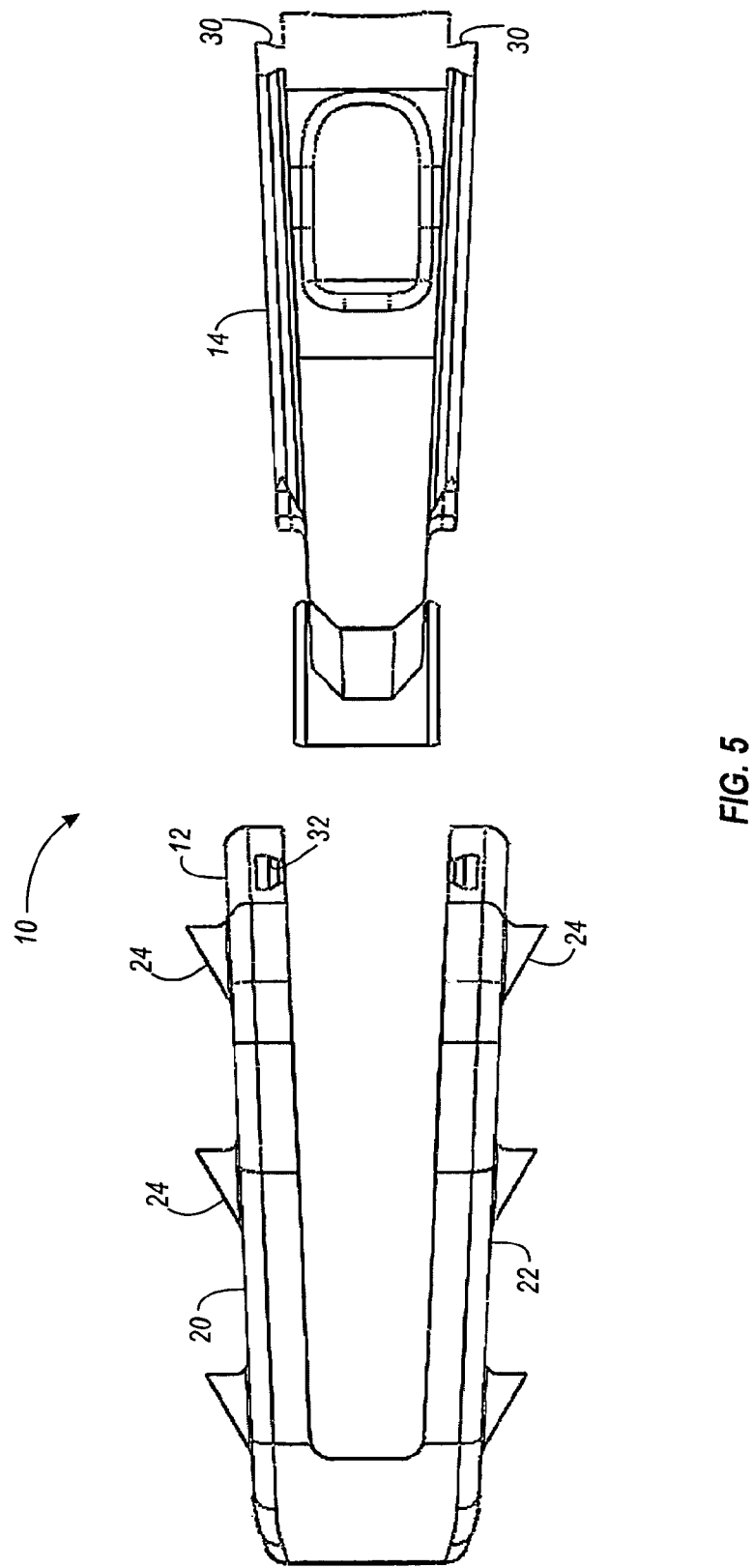
FIG. 5 is an exploded side view of the interbody fusion device 10.

The interbody fusion device 10 is designed to be installed between the end plates of two adjacent vertebrae to facilitate the fusion of the vertebrae. The interbody fusion device 10, having the appropriate lordosis or kyphosis, provides load bearing support as well as the proper spacing between the vertebrae while fusion of the vertebrae takes place. When in use, the interbody fusion device 10 is positioned between the end plates of the vertebrae within the vertebral body in the area usually occupied by the intervertebral disc.

The interbody fusion device 10 is formed by a first piece 12 and a second piece 14, inserted within the first piece 12. In one example, the first and second pieces 12 and 14 are comprised of different materials. In one example the first piece 12 is made from titanium, which gives the interbody fusion device 10 strength. In one example, the second piece 14 is made from a biocompatible synthetic polymer, such as being made from a polyetheretherketone (PEEK®). If desired, the second piece 14 may include radio opaque markers that will show up in an X-ray, although the first piece 12 (if made of titanium) will also show up in an X-ray. Note that the first and second pieces may also be comprised of other materials.

The first piece 12 has upper and lower surfaces 20 and 22, which are configured to engage the endplates of the vertebrae. A plurality of barbed teeth 24 extend from the upper and lower surfaces 20 and 22 to prevent anterior expulsion of the interbody fusion device 10. The barbed teeth 24 are configured to dig into the bone, resisting anterior forces, and provide immediate, mechanical post-operative resistance to anterior expulsion.

As mentioned above, the second piece 14 is designed to fit within the first piece 12. In the examples shown, the first and second pieces 12 and 14 include sliding joints (similar to dovetail joints) to strengthen the union of the first and second pieces. The second piece 14 has two protrusions 30 shaped to fit within matching grooves 32 formed in the first piece 12. The second piece 14 also includes a plurality of angled protrusions 31 that lock into matching indentations formed in the first piece 12.

As shown in the figures, an opening 28 is formed in the interbody fusion device 10. The opening 28 provides a graft volume that can be filled with a prepared material that will help to facilitate fusion of the vertebrae through the opening 28. Examples of a material include bone material, bone marrow, bone substitutes (β-TCP, HA), bone morphonogenic protein (BMP), autologous stem cells, osteogenic growth factors, or other materials or combinations thereof.

If desired, one or more openings can be formed in the interbody fusion device 10 to facilitate instrumentation devices. In the example shown in the figures, two lateral scallops 34 are formed on opposite sides of the second piece 14. A central scallop 36 is formed on the front surface of the second piece 14. The two lateral scallops 34 facilitate gripping the fusion device 10 using a bi-fed instrument grip (not shown), such as a Kerrison-style implant holder or a forceps style implant holder. The central scallop 36 facilitates manipulation of the fusion device 10 using an implant pusher (not shown). An implant pusher would typically have a dimple formed that matches the central scallop 36 to prevent slippage of the implant pusher.

As mentioned above, in one example, the first piece 12 can be comprised of titanium. To help the fixation of the fusion device 10 to the vertebrae, the upper and lower surfaces 20 and 22 of the first piece 12 can be at least partially textured or coated with a porous, biocompatible material or texturing that promotes bone in-growth to provide fixation to the bone. The titanium may also be coated with hydroxyapatite (HA) (or other material) to promote osseointegration. Likewise, the surface of the titanium can be in the form of porous titanium to permit bone ongrowth. The second piece 14 may also be at least partially textured or coated with a porous, biocompatible material or texturing that promotes bone in-growth to provide fixation to the bone.

Following is a description illustrating how an interbody fusion device may be used in a spinal fusion procedure. First, the vertebral body is prepared for the implant. This preparation may include cleaning out the nucleus pulposus and scraping the vertebral bodies. If desired, a prepared material can be placed in the opening 28 of the fusion device 10 to promote fusion. The implant is inserted between the adjacent vertebrae using the appropriate instrumentation, as desired.

In the preceding description, the devices and methods are described with reference to exemplary embodiments thereof. Various modifications and changes may be made thereto without departing from the broader spirit and scope of the disclosure.

What is claimed is:

1. An interbody fusion device for fusion of vertebrae, comprising: a first piece made of titanium having upper and lower surfaces, wherein the upper and lower surfaces of the first piece are configured to engage the endplates of two opposing vertebrae, the upper and lower surfaces including a plurality of barbed teeth configured to engage an endplate, and a second piece, the first piece including an inner void area configured to receive the second piece, wherein the second piece is configured to engage the first piece to slide over inner surfaces of the first piece and become seated and mated within the first piece, such that the entire second piece is located within the first piece, and wherein the second piece includes two protrusions located on the upper surface of the second piece and two protrusions located on the lower surface of the second piece, wherein each of the protrusions has a width that is shorter than its length, and the protrusions are shaped to fit within matching grooves that are located on the inner surfaces of the first piece, the grooves having a complementary shape to the protrusions such that the protrusions are dovetailed within the grooves when the first and second pieces are mated, and wherein the second piece includes a plurality of angled protrusions that lock into the matching indentations formed into the first piece, the first and second pieces when mated forming the assembled interbody fusion device that fits between two vertebrae.

2. The device of claim 1, wherein the second piece is made of a polymer.

3. The device of claim 1, wherein the second piece is made of PEEK.

4. The device of claim 1, wherein the outer surfaces of the first piece have been coated with a material for bone ingrowth.

5. The device of claim 1, wherein the first and second pieces mate to form a single piece that includes an opening.

6. The device of claim 5, wherein the opening is filled with material to facilitate fusion of vertebrae through the opening.

7. The device of claim 1, including instrumentation openings to facilitate instrumentation devices.

8. The device of claim 7, including lateral scallops on opposite sides of the second piece for interaction with instrumentation devices.

9. A method of fusing vertebrae, comprising:
removing at least a portion of a disc between first and second vertebrae, providing an interbody fusion device which comprises a first piece made of titanium having upper and lower surfaces, wherein the upper and lower surfaces of the first piece are configured to engage the endplates of two opposing vertebrae, the upper and lower surfaces including a plurality of barbed teeth configured to engage an endplate, the first piece including an inner void area configured to receive a second piece, the second piece configured to engage the first piece to slide over inner surfaces of the first piece become seated and mated within the first piece, such that the entire second piece is located within the first piece, and wherein the second piece includes two protrusions located on the upper surface of the second piece and two protrusions located on the lower surface of the second piece, wherein each of the protrusions has a width that is shorter than its length, and the protrusions are shaped to fit within matching grooves that are located on the inner surfaces of the first piece, the grooves having a complementary shape to the protrusions such that the protrusions are dovetailed within the grooves when the first and second pieces are mated, and wherein the second piece includes a plurality of angled protrusions that lock into the matching indentations formed into the first piece, the first and second pieces when mated forming the assembled interbody fusion device that fits between two vertebrae,
inserting the first piece between the vertebrae,
packing the second piece with material to facilitate fusion of the first and second vertebrae, and
inserting the second piece fully into the first piece to mate the first and second pieces.

10. A method of manufacturing an interbody fusion device, comprising: forming a first piece made of titanium having upper and lower surfaces, wherein the upper and lower surfaces of the first piece are configured to engage the endplates of two opposing vertebrae, the upper and lower surfaces including a plurality of barbed teeth configured to engage an endplate, the first piece including an inner void area configured to receive a second piece, forming the second piece configured to engage the first piece to slide over inner surfaces of the first piece become seated and mated within the first piece, such that the entire second piece is located within the first piece, and wherein the second piece includes two protrusions located on the upper surface of the second piece and two protrusions located on the lower surface of the second piece, wherein each of the protrusions has a width that is shorter than its length, and the protrusions are shaped to fit within matching grooves that are located on the inner surfaces of the first piece, the grooves having a complementary shape to the protrusions such that the protrusions are dovetailed within the grooves when the first and second pieces are mated, and wherein the second piece includes a plurality of angled protrusions that lock into the matching indentations formed into the first piece, the first and second pieces when mated forming the assembled interbody fusion device that fits between two vertebrae.

* * * * *